(12) United States Patent
McEwen et al.

(10) Patent No.: US 12,082,823 B1
(45) Date of Patent: Sep. 10, 2024

(54) SAFE SELF-LOOSENING TOURNIQUET CUFF FOR ENABLING OPTIMIZATION OF TOURNIQUET TIME

(71) Applicant: Western Clinical Engineering Ltd., Vancouver (CA)

(72) Inventors: James A. McEwen, Vancouver (CA); Tom Yu Chia Lai, Vancouver (CA); Michael Jameson, North Vancouver (CA); Matthew Yee, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 0 days.

(21) Appl. No.: 18/418,932

(22) Filed: Jan. 22, 2024

(51) Int. Cl.
| | |
|---|---|
| *A61B 17/135* | (2006.01) |
| *A61F 2/00* | (2006.01) |
| *A61B 17/00* | (2006.01) |
| *A61B 90/00* | (2016.01) |

(52) U.S. Cl.
CPC .......... *A61B 17/135* (2013.01); *A61F 2/0013* (2013.01); *A61B 2017/00862* (2013.01); *A61B 2090/032* (2016.02)

(58) Field of Classification Search
CPC ........ A61B 17/135; A61B 2017/00862; A61B 2090/032; A61F 2/0013
See application file for complete search history.

(56) References Cited

U.S. PATENT DOCUMENTS

| | | | | |
|---|---|---|---|---|
| 3,633,567 A | * | 1/1972 | Sarnoff ............. | A61B 5/02141 600/499 |
| 5,702,042 A | * | 12/1997 | Peacock .................... | A45F 3/00 224/660 |
| 9,295,474 B2 | * | 3/2016 | Heston ................... | A61B 90/00 |

* cited by examiner

Primary Examiner — Julian W Woo
(74) Attorney, Agent, or Firm — Klarquist Sparkman, LLP (57) ABSTRACT

A self-loosening tourniquet cuff for optimization of tourniquet time comprises an inflatable bladder, an elastic self-loosening tether and an inelastic safety tether. The bladder has a length between first and second ends sufficient for the bladder to encircle a patient's limb and overlap itself. The elastic self-loosening tether has an elastic member non-releasably attached to the bladder near the first end and a securing member non-releasably attached to the elastic member and adapted to releasably attach to the bladder when overlapped to establish a first bladder overlap length. The elastic member is adapted for stretching to establish a second bladder overlap length less than the first bladder overlap length. The inelastic safety retainer retains the bladder around the patient's limb near the second bladder overlap length when the bladder is inflated to a pressure sufficient to stop the flow of arterial blood into the patient's limb distal to the bladder.

14 Claims, 6 Drawing Sheets

SAFE SELF-LOOSENING TOURNIQUET CUFF FOR ENABLING OPTIMIZATION OF TOURNIQUET TIME

BACKGROUND

Typical surgical tourniquet systems in the prior art include a tourniquet cuff which is applied by a physician, nurse or surgical technologist to encircle a location of a patient's limb by overlapping and securing the cuff to itself. A tourniquet instrument is releasably connected to an inflatable bladder within the tourniquet cuff through a length of tubing, thereby establishing a gas-tight passageway between the inflatable bladder and the tourniquet instrument. The tourniquet instrument contains a pressurized gas source which is used to inflate and regulate the pressure of gas in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. Nos. 4,469,099, 4,479,494, 5,439,477 and McEwen and Jameson in U.S. Pat. Nos. 5,556,415 and 5,855,589.

Basic research findings and many clinical studies and observations over many years have clearly established both the benefits and the risks associated with the usage of surgical tourniquets.

Benefits of using surgical tourniquet systems include establishment of a clear, dry bloodless field for improved visualization, better control of blood loss, and faster procedural completion time for improved surgical efficiency and intraoperative workflow. Tourniquet related risks may be generally grouped into two categories: pressure-related and time-related. Pressure-related risk of injury has been shown to be related to the level of tourniquet pressure employed, and to the pressure gradients applied by specific types of tourniquet cuffs to underlying limbs. Time-related risk of injury has been shown to be related to the sustained duration of tourniquet pressurization. Typically, a tourniquet cuff is applied and inflated at the start of the surgical procedure, and deflated and removed at the end of the surgical procedure.

Pressure-related risk of injury has been minimized through the invention of (1) modern microprocessor tourniquet systems, allowing more accurate and automatic pressure control (McEwen, U.S. Pat. No. 4,469,099), (2) setting a tourniquet pressure based on the patient's limb occlusion pressure, thereby applying a personalized minimum effective occlusion pressure (McEwen, U.S. Pat. No. 8,425,426), and (3) wide contour tourniquet cuffs that substantially reduce pressures required to create a bloodless surgical field distal to the inflated cuff (McEwen, U.S. Pat. No. 7,758,607).

One pathway to minimize time-related risk of injury while retaining the benefits of tourniquet use is to apply the tourniquet cuff at the start of the surgical procedure, but only inflate it when it is needed; for example, when improved visualization is required, or for a particular part of the surgical procedure where a bloodless field is critical, such as cementation of an implant. This approach can optimize and dramatically decrease the overall tourniquet inflation time, thereby minimizing the risk of time-related tourniquet injury.

However, applying a tourniquet cuff at beginning of a surgical procedure and inflating it at a later time during the procedure can create a hazard. An over-tightened, uninflated tourniquet cuff can apply sufficient pressure to the limb prior to inflation to cause tissue congestion in the limb distal to the tourniquet cuff by restricting venous outflow while still allowing arterial inflow. Thus, the application pressure arising from a tightly applied and uninflated tourniquet cuff can lead to venous congestion of the limb distal to the cuff, hemorrhagic infiltration of the nerves, and oozing of blood into the surgical field. Venous congestion can be detected non-invasively by plethysmography. Marcelli, E., Cercenelli, L., Bortolani, B., Marini, S., Arfilli, L., Capucci, A., & Plicchi, G. (2021), A novel non-invasive device for the assessment of central venous pressure in hospital, office and home (Medical Devices: Evidence and Research, 141-154) and Wilkinson, I. B., & Webb, D. J. (2001), Venous occlusion plethysmography in cardiovascular research: methodology and clinical applications (British Journal of Clinical Pharmacology, 52(6), 631.)

Therefore, in order to safely optimize tourniquet time by applying a tourniquet cuff and inflating it at a later time, the tourniquet cuff must be applied at a snugness sufficient for the cuff to remain stable on the limb in both inflated and uninflated states and which does not substantially restrict venous drainage.

However, most tourniquet cuffs of prior art are often applied with inconsistent snugness. This is because the snugness of a tourniquet cuff application is highly dependent on the skill and experience of the applicator (physician, nurse, or surgical technologist), the patient's limb characteristics (e.g. muscle tone, limb shape), and the tourniquet cuff design (e.g. cylindrical or contour cuff shape; tie ribbons or application handle to facilitate tightening of cuff during application). Furthermore, the current recommended method to assess the adequacy of tourniquet cuff application snugness is flawed. The Association of Surgical Technologists (AST) and most tourniquet cuff manufacturers recommend using a 'finger test' to determine the snugness of the tourniquet cuff application. AST's "Guideline for Best Practices for Safe Use of Pneumatic Tourniquets" states "a securely applied cuff should allow the CSR [Certified Surgical Technologist] to easily slide two fingers under the proximal and distal cuff edges. If only one finger can slide under, the cuff is too tight; if three fingers can be slid under, the cuff is too loose." The 'finger test' is flawed due to the following three reasons. First, since most limbs are tapered, the number of fingers that can slide under the proximal and distal edges of the cuff often are not equivalent. Second, for very tapered limbs, a large gap between the distal edge of the cuff and the limb may be unavoidable, resulting in a gap that can fit three or more fingers. Third, the degree at which sliding the finger(s) under the tourniquet cuff is considered 'easily' is subjective. Since a limb is made up of soft tissues, the applicator can likely always slide one to three fingers under the tourniquet cuff at varying degrees of ease.

For these reasons above, in an attempt to prevent inadvertent venous occlusion, at least one tourniquet cuff in the prior art (Heston, U.S. Pat. No. 9,295,474) includes a tightness indicator composed of a resiliently extendable member attached to an inelastic retainer. When the resiliently extendable member of Heston '474 is fully extended and the inelastic retainer is in the taut condition, the user can wrap and secure the inelastic retainer around the limb to apply a predetermined amount of force sufficient to secure the cuff to the limb. However, the tightness indicator of Heston '474 has two limitations. First, the tightness indicator only provides an indication up to a point where the resiliently extendable member is fully extended; thus, a user may continue to increase tightness beyond this point without any further indication, allowing an overtightened cuff to still be applied around the limb resulting in a venous congestion hazard to the patient. Second, the tightness indicator of Heston '474 does not self-loosen to reduce the application pressure applied to the limb to achieve an applied uninflated pressure sufficient to prevent venous congestion. The tightness indicator of Heston '474 can only function as an indicator and requires manual operation, i.e. it relies on the user to adjust the application tightness based on the indicator. Because of these two significant limitations, Heston '474 does not and cannot safely self-loosen to prevent the overtightened cuff from being secured around the limb.

Thus, there is a need for a safe self-loosening tourniquet cuff that can adapt to the tightness applied during the cuff application process to safely self-loosen and prevent the overtightened cuff from being secured around the limb, thereby minimizing the risk of venous congestion and enabling optimization of tourniquet time by allowing a cuff to be safely applied at the start of surgery and to remain uninflated until it is needed.

SUMMARY

Described below are implementations of methods and apparatus that address shortcomings in the prior art.

According to a first implementation, a safe self-loosening tourniquet cuff apparatus for enabling optimization of tourniquet time comprises an inflatable bladder having a length dimension between a first bladder end and a second bladder end sufficient for the inflatable bladder to encircle a patient's limb circumference at a limb location and to overlap itself, an elastic self-loosening tether and an inelastic safety retainer. The elastic self-loosening tether comprises an elastic member non-releasably attached to the inflatable bladder near the first bladder end and a securing member non-releasably attached to the elastic member and adapted to releasably attach to the inflatable bladder when overlapped to establish a first bladder overlap length, wherein the elastic member is adapted for stretching to establish a second bladder overlap length less than the first bladder overlap length and greater than zero. The inelastic safety retainer is adapted for retaining the inflatable bladder around the patient's limb near the second bladder overlap length when the inflatable bladder is inflated to a pressure sufficient to stop the flow of arterial blood into the patient's limb distal to the bladder.

In some implementations, the inelastic safety retainer is further adapted to be operable independently of the elastic self-loosening tether.

In some implementations, the inelastic safety retainer is comprised of flexible material that is substantially inelastic when the retained inflatable bladder is inflated to a pressure of less than 600 mmHg.

In some implementations, the elastic member is comprised of flexible material having an elastic physical property selected to enable substantially elastic stretching between the first bladder overlap length and the second bladder overlap length.

In some implementations, the inelastic safety retainer is superposed on the securing member of the elastic self-loosening tether when the inflatable bladder is retained.

According to another implementation, a safe self-loosening tourniquet cuff assembly, comprises a cuff element having a length dimension between a first end and a second end that is greater than a patient's limb circumference at a limb location and sufficient for the cuff element to encircle the patient's limb and to overlap upon itself, an elastic member non-releasably attached to the cuff member near the first end, a securing member non-releasably attached to the elastic member and adapted for releasable attachment to the cuff element when overlapped to establish a first cuff circumference less than the limb circumference, thereby applying a first application pressure to the encircled limb by deforming soft tissue of the encircled limb, wherein the elastic member is adapted to stretch and thereby self-loosen the cuff element to apply a second application pressure to the encircled limb that is less than the first application pressure and greater than a predetermined minimum application pressure, and an inelastic safety retainer operable independently of the elastic member to retain the cuff element at the second application pressure.

The cuff element can include an inflatable bladder, and the inelastic safety retainer is further operable to retain the cuff element in an overlapped state when the inflatable bladder is inflated to a pressure that is less than a predetermined maximum pressure. The predetermined maximum pressure can be 600 mmHg.

The elastic member can comprise flexible material selected to enable elastic stretching to establish the second application pressure.

According to another implementation, a safe self-loosening tourniquet cuff apparatus for enabling optimization of tourniquet time comprises an inflatable bladder having a length dimension between a first bladder end and a second bladder end that is greater than a patient's limb circumference at a limb location, an elastic self-loosening tether and an inelastic safety retainer. The elastic self-loosening tether includes an elastic component non-releasably attached to the inflatable bladder near the first bladder end and a securing component non-releasably attached to the elastic component and adapted to releasably attach to the inflatable bladder to establish a first bladder circumference that is less than the limb circumference at the limb location. The elastic component is adapted to stretch to establish a second bladder circumference greater than the first bladder circumference and at most equal to the limb circumference at the limb location. The inelastic safety retainer is adapted to releasably retain the inflatable bladder near the second bladder circumference when the inflatable bladder is inflated to a pressure sufficient to stop the flow of arterial blood into the patient's limb distal to the bladder.

The inelastic safety retainer can be further adapted for operation independently of the elastic self-loosening tether. The inelastic safety retainer can comprise flexible material that is substantially inelastic when the inflatable bladder is inflated to a pressure of less than 600 mmHg.

The elastic member can comprise flexible material having an elastic physical property selected to enable substantially elastic stretching between the first bladder circumference and the second bladder circumference.

According to another implementation, a method for safe self-loosening of a tourniquet cuff comprises positioning a cuff element at a limb location on a patient, the cuff element having a length dimension between a first end and a second end greater than a limb circumference at the limb location and sufficient for the cuff element to encircle the patient's limb with the first end overlapped over the second end, wherein the cuff member has an elastic member non-releasably attached near the first end and a securing member non-releasably attached to the elastic member, releasably attaching the securing member to the cuff element to establish a first cuff circumference less than the limb circumference, thereby applying a first application pressure to the limb by deforming soft tissue of the limb, allowing the elastic member to stretch and thereby self-loosen the cuff element, wherein the cuff element in a self-loosened state applies a second application pressure to the limb that is less than the first application pressure and greater than a predetermined minimum application pressure, and extending an inelastic safety retainer over the first end and attaching the inelastic safety retainer to the cuff element for retaining the cuff element at substantially the second application pressure.

DETAILED DESCRIPTION

Figure 1A:
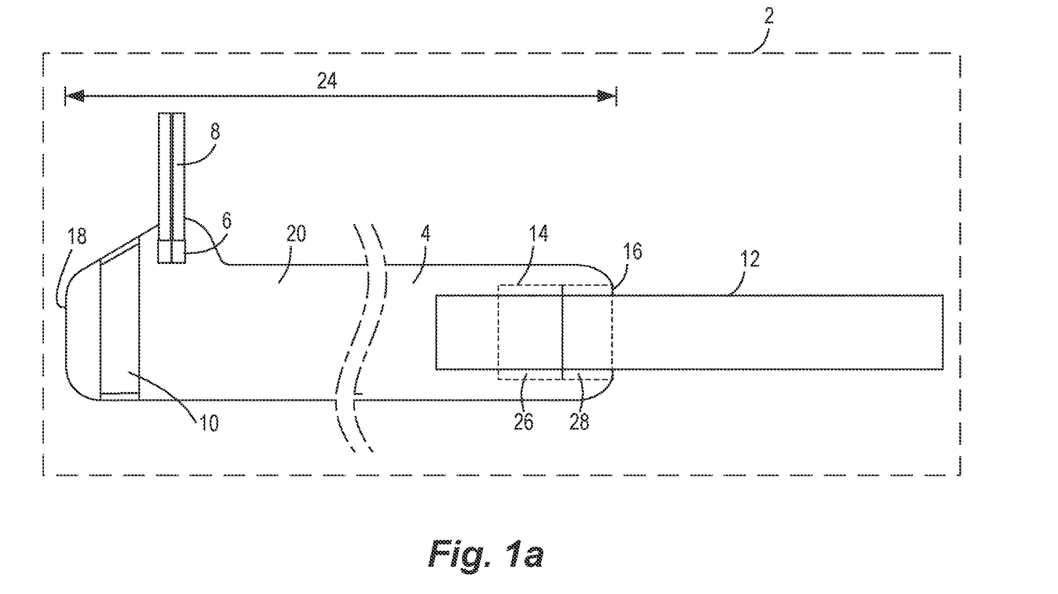
FIGS. 1a and 1b are top and side views of the preferred embodiment, respectively.
Figure 1B:
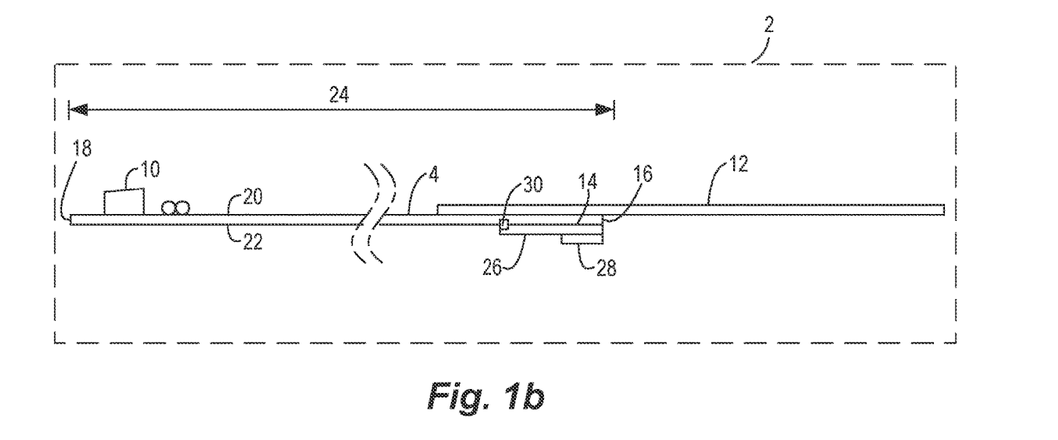

Described below are implementations of a safe self-loosening tourniquet cuff and associated methods. FIGS. 1a and 1b are top and side views, respectively, of a preferred embodiment of the tourniquet cuff shown laid flat. Safe self-loosening tourniquet cuff 2 includes inflatable bladder 4, port 6, tubing 8, application handle 10, inelastic safety retainer 12, and elastic self-loosening tether 14.

Inflatable bladder 4 has a first bladder end 16, a second bladder end 18, a top surface 20, and a bottom surface 22. The length between first bladder end 16 and second bladder end 18 defines bladder length 24 of inflatable bladder 4.

Inflatable bladder 4 is pneumatically connected to tubing 8 through port 6. Tubing 8 may be connected to a pneumatic tourniquet instrument which can supply pressurized air to inflatable bladder 4, as described in prior art. The preferred embodiment has a dual-port design with a single bladder. The same principles can be applied, however, to a single-port design, or a multi-bladder design such as those used for Bier Block or Intravenous Regional Anesthesia.

Application handle 10 is affixed, i.e., non-releasably attached, to top surface 20 of inflatable bladder 4 near second bladder end 18. Application handle 10 facilitates the application of inflatable bladder 4 around a patient's limb, as described by McEwen in U.S. Pat. No. 9,011,483. Alternatively, a tie strap as described by McEwen in U.S. Pat. No. 7,758,607 may be used instead of application handle 10. As used herein, non-releasably attached means under general clinical conditions, the user cannot separate the non-releasable attachment without destroying it. In the preferred embodiment, application handle 10 is attached to inflatable bladder 4 through sewing.

Inelastic safety retainer 12 is attached to top surface 20 of inflatable bladder 4 near first bladder end 16. Inelastic safety retainer 12 and top surface 20 of inflatable bladder 4 are formed of materials such that when inflatable bladder 4 overlaps upon itself, inelastic safety retainer 12 can be releasably attached to top surface 20 of inflatable bladder 4 to secure inflatable bladder 4 around a patient's limb. Inelastic safety retainer 12 is composed of flexible material that is substantially inelastic when subjected to a force typical of a pneumatic tourniquet apparatus, up to an inflated cuff pressure of 600 mmHg. When inelastic safety retainer 12 is under tension, such as during the tightening of inflatable bladder 4 around a patient's limb, inelastic safety retainer 12 maintains its shape (length) in the direction of the tension. In the preferred embodiment, inelastic safety retainer 12 consists of a Velcro®-hook type material and top surface 20 of inflatable bladder 4 consists of a Velcro®-loop type material.

Elastic self-loosening tether 14 is non-releasably attached to bottom surface 22 of inflatable bladder 4 near first bladder end 16. Elastic self-loosening tether 14 is comprised of elastic member 26 and securing member 28. Elastic member 26 is non-releasably attached to bottom surface 22 of inflatable bladder 4 near first bladder end 16 at attachment point 30. In an alternate embodiment, the opposite end of elastic member 26 may also be attached to bottom surface 22 of inflatable bladder 4 near first bladder end 16 to keep elastic member 26 flush with bottom surface 22 of inflatable bladder 4. Securing member 28 is non-releasably attached to the elastic member 26. Attachment of the securing member 28 to elastic member 26 and elastic member 26 to inflatable bladder 4 may be accomplished through welding, stitching, adhesive or other attachment methods. Securing member 28 is formed of material such that when inflatable bladder 4 overlaps upon itself, securing member 28 can be releasably attached to top surface 20 of inflatable bladder 4. In the preferred embodiment, securing member 28 consists of a Velcro®-hook type material.

Elastic member 26 is composed of flexible material having physical properties that include elasticity (stretch). Elastic member 26 stretches substantially elastically when subjected to forces typical during the application of a pneumatic tourniquet apparatus. When an external force is pulling attachment point 30 away from securing member 28, elastic member 26 elongates. When the external force is removed, elastic member 26 substantially returns to its original length. Securing member 28 is tethered to attachment point 30 through elastic member 26. In the preferred embodiment, elastic member 26 is made of elastic webbing and is adapted to stretch when under tension. It will be apparent to those skilled in the art that other materials can be used for elastic member 26, such as thermoplastic film. It will also be apparent to those skilled in the art that securing member 28 may releasably attach to top surface 20 of inflatable bladder 4 by other means, such as adhesive.

Figure 2A:
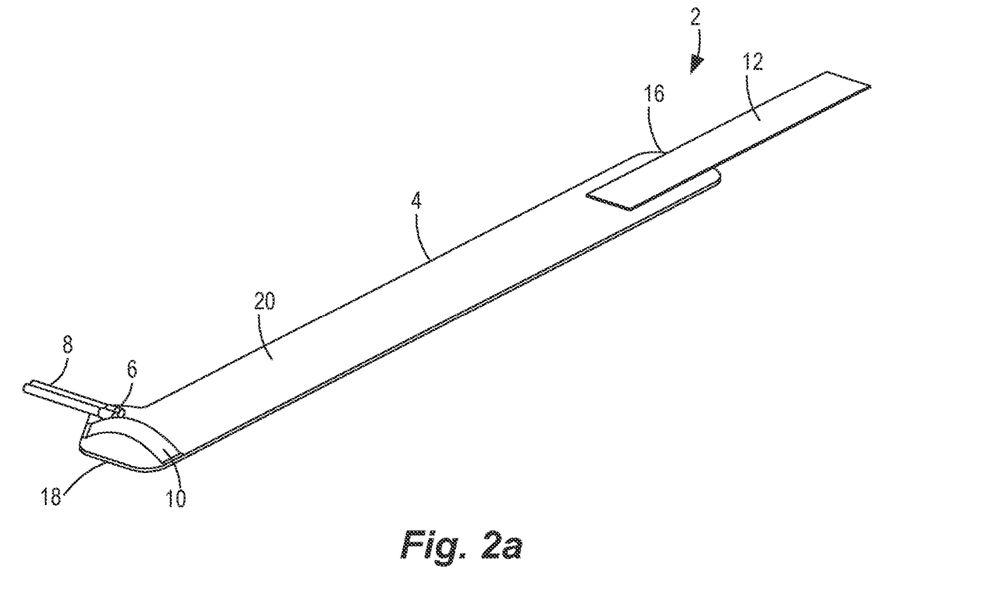
FIGS. 2a and 2b are the perspective top and bottom views of the preferred embodiment, respectively.
Figure 2B:
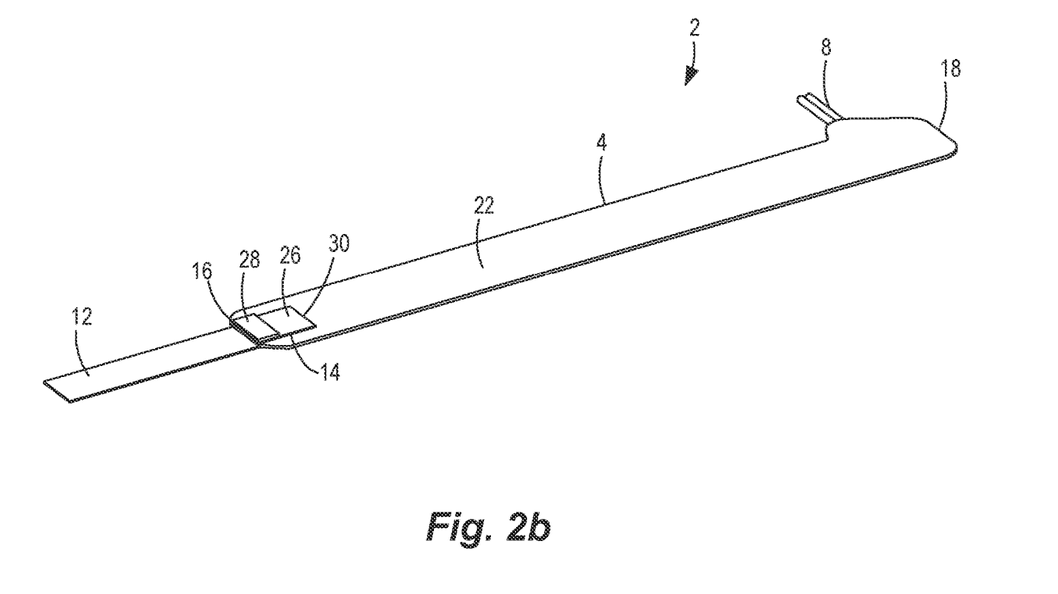

FIGS. 2a and 2b show perspective views of the top and the bottom of the cuff 2.

FIGS. 3a, 3b, 3c, and 3d show cross-sectional side views of the cuff 2 as applied to encircle a patient's limb 32. Inflatable bladder 4 is selected (or sized) such that bladder length 24 is sufficient for inflatable bladder 4 to overlap upon itself to encircle the patient's limb circumference at a limb location of limb 32.

Corresponding perspective views of FIG. 3a-3d are shown in FIG. 4a-4d, respectively.

Figure 3A:
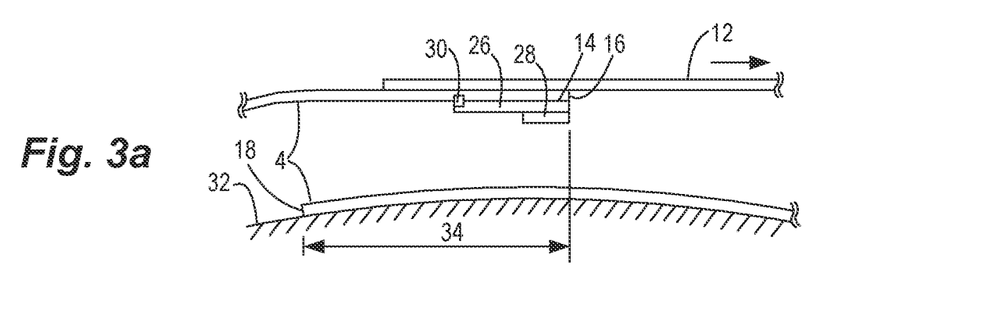
FIGS. 3a, 3b, 3c, and 3d are side views of the preferred embodiment applied to the cross-section of a limb.
Figure 4A:
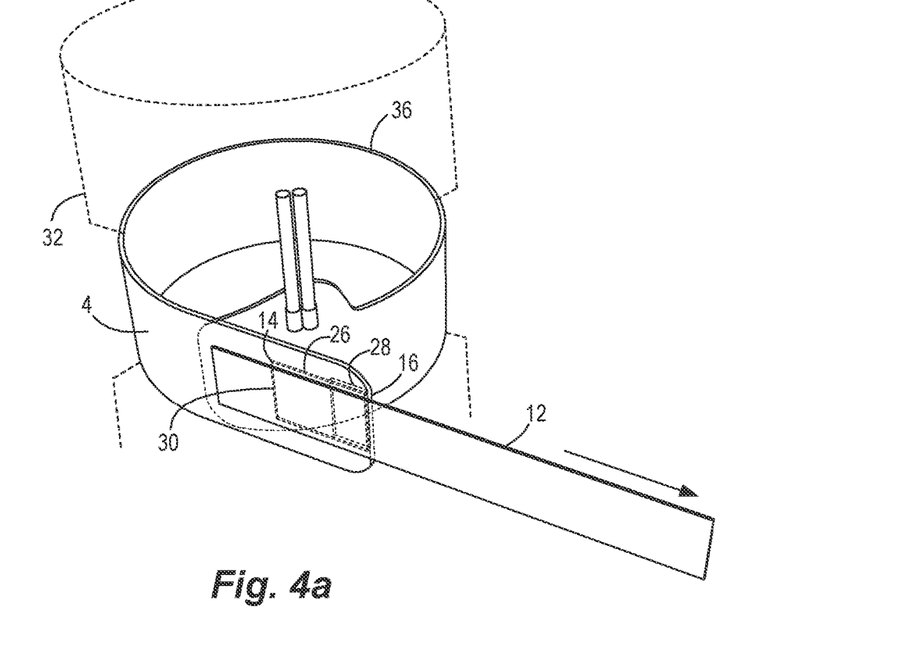
FIGS. 4a, 4b, 4c, and 4d are corresponding perspective views of FIGS. 3a, 3b, 3c, and 3d.

FIG. 3a and FIG. 4a show the first step in the application of the preferred embodiment. A user encircles limb 32 with inflatable bladder 4 such that inflatable bladder 4 overlaps upon itself. The user then tightens inflatable bladder 4 around limb 32. For example, the user can pull application handle 10 (see, e.g., FIGS. 1a, 1b and 2a; not shown in some figures for clarity) and inelastic safety retainer 12 in opposite directions to tighten inflatable bladder 4 around limb 32.

The tightening step causes inflatable bladder 4 to:
(a) overlap upon itself by a first bladder overlap length 34 equal to the length between first bladder end 16 and second bladder end 18 of the overlapped inflatable bladder 4,
(b) establish a first bladder circumference 36 equal to bladder length 24 minus first bladder overlap length 34, (c) deform the portion of limb 32 encircled by inflatable bladder 4, and thereby to (d) apply a first application pressure onto limb 32.

Figure 3B:
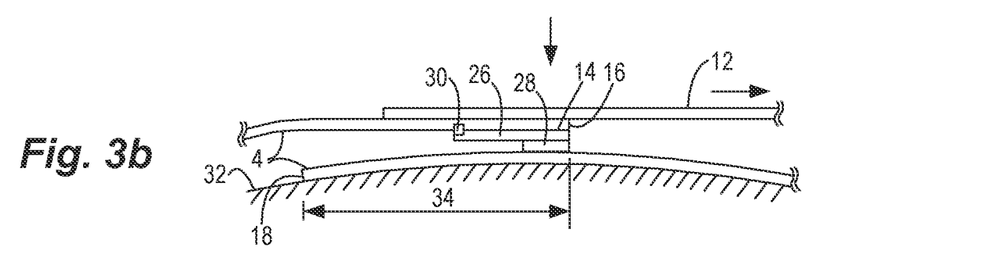
Figure 4B:
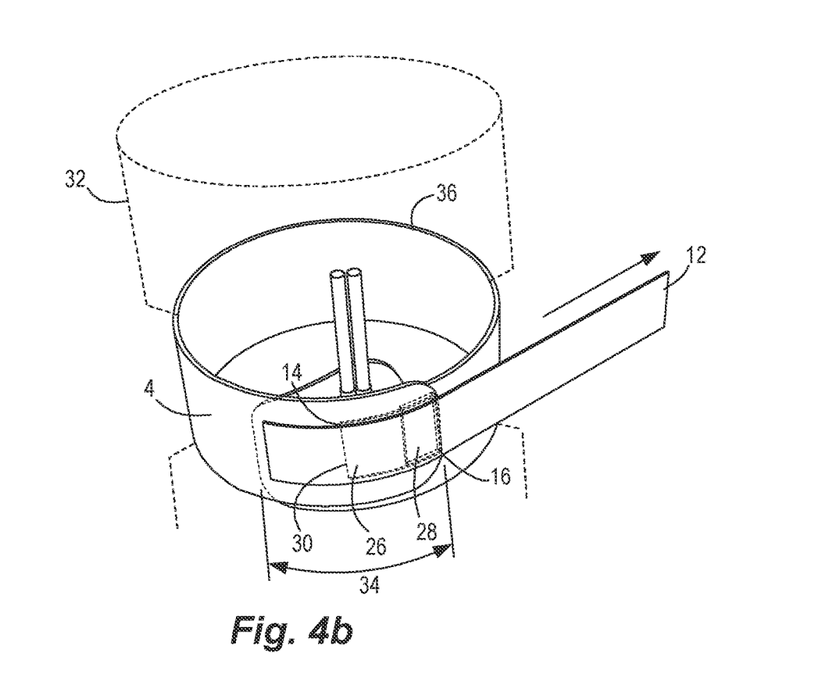

FIG. 3b and FIG. 4b show the second step in the application of the preferred embodiment while tightening. The user releasably attaches securing member 28 to top surface 20 of inflatable bladder 4, with the overlapped inflatable bladder 4 having first bladder overlap length 34, establishing first bladder circumference 36, and applying the first application pressure into limb 32.

Figure 3C:
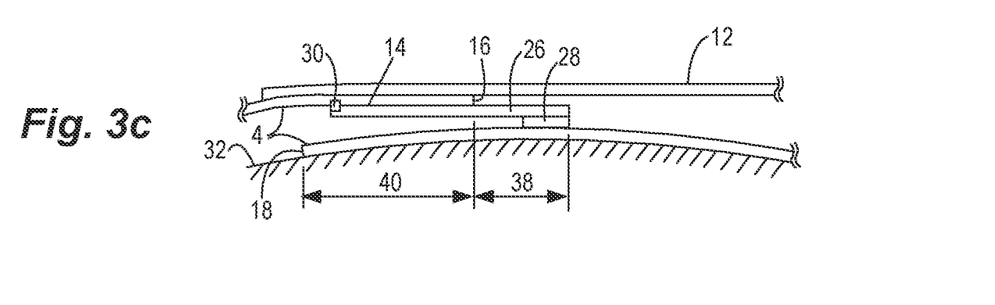
Figure 4C:
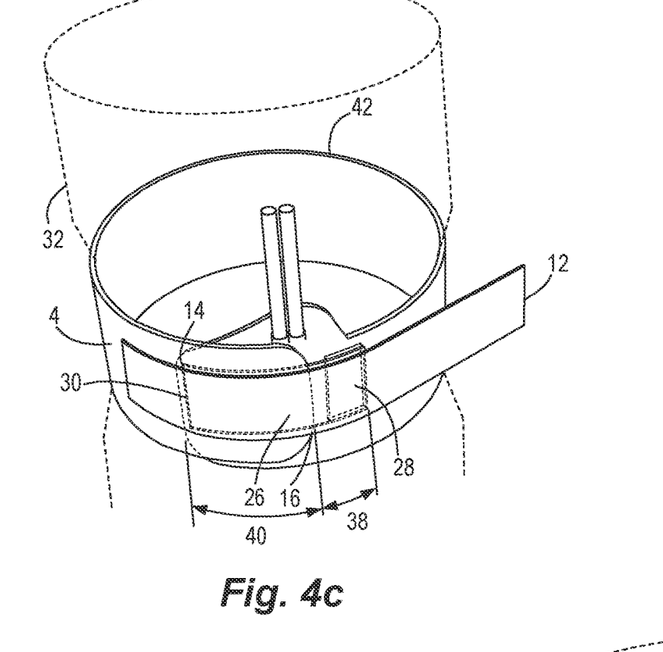

FIG. 3c and FIG. 4c show the third step in the application of the preferred embodiment. The user stops pulling application handle 10 (not shown in figure for clarity) and inelastic safety retainer 12 in opposite directions to tighten inflatable bladder 4 around limb 32. As this external force is removed, limb 32 tends to return to its non-deformed shape which causes:

(a) elastic member 26 to stretch between first bladder overlap length 34 and second bladder overlap length 40, and (b) inflatable bladder 4 to self-loosen by self-loosened distance 38 to establish a second bladder overlap length 40, establish a second bladder circumference 42, and apply a second application pressure into limb 32.

Second bladder overlap length 40 is equal to the length between first bladder end 16 and second bladder end 18 of the overlapped, now self-loosened inflatable bladder 4. Second bladder overlap length 40 is less than first bladder overlap length 34 and greater than zero.

Second bladder circumference 42 is equal to bladder length 24 minus second bladder overlap length 40. Second bladder circumference 42 is greater than first bladder circumference 36 and at most equal to the patient's limb circumference at the limb location of limb 32 prior to cuff application.

Second application pressure is less than the first application pressure and greater than a predetermined minimum application pressure. In the preferred embodiment the predetermined minimum application pressure is 0 mmHg.

Self-loosened distance 38 is equal to first bladder overlap length 34 minus second bladder overlap length 40. Self-loosened distance 38 is also equal to second bladder circumference 42 minus first bladder circumference 36.

Elastic member 26 is selected to have characteristics such that the self-loosened distance 38 is correlated with the magnitude of the first application pressure applied into limb 32 such that the second application pressure applied into limb 32 is less than a predetermined pressure. In the preferred embodiment, the predetermined pressure is less than the pressure that may lead to venous congestion.

Figure 3D:
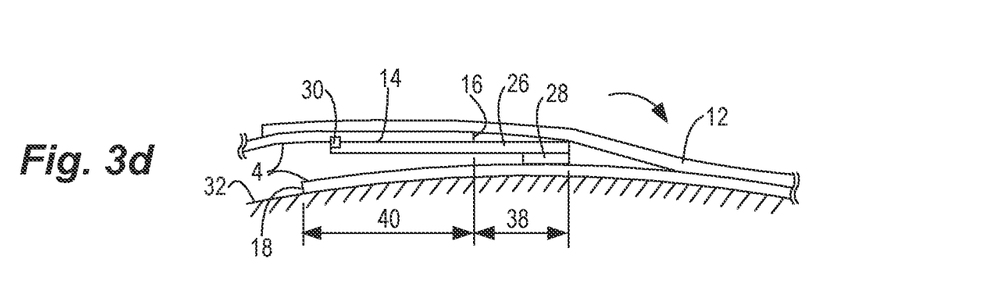
Figure 4D:
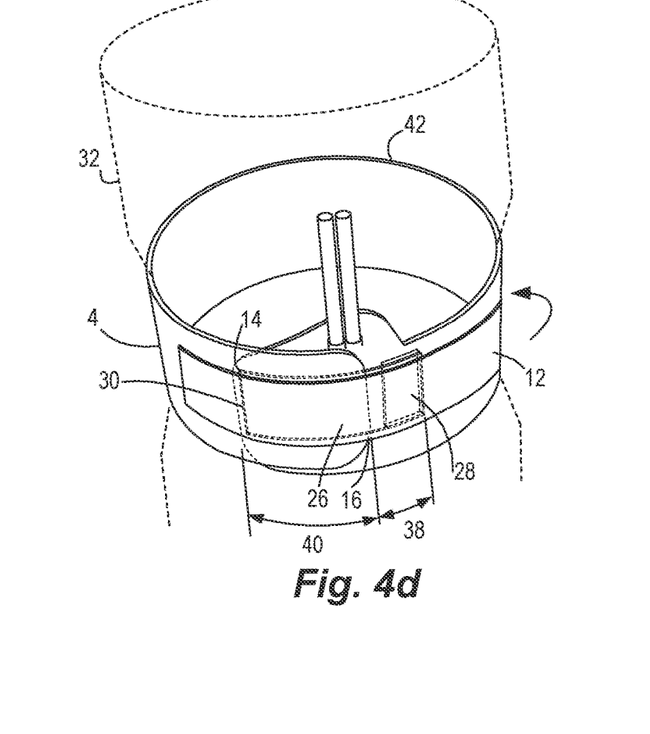

FIGS. 3d and 4d show the final step in the application of the preferred embodiment. The user releasably attaches inelastic safety retainer 12 to top surface 20 of the self-loosened inflatable bladder 4 to retain the self-loosened inflatable bladder 4 around limb 32 having near second bladder overlap length 40, establishing near second bladder circumference 42 and applying near the second application pressure into limb 32. Inelastic safety retainer 12 is operable independently of elastic self-loosening tether 14. In the preferred embodiment, inelastic safety retainer 12 superposes the releasably attached securing member 28, thereby enabling inflatable bladder 4 encircling limb 32 to be inflated to a pressure sufficient to stop the flow of arterial blood distal to the limb encircled by the bladder.

When inflatable bladder 4 is inflated to a pressure sufficient to stop the flow of arterial blood into limb 32 distal to inflatable bladder 4, inelastic retainer 12 retains the self-loosened inflatable bladder 4 around limb 32 having near second bladder overlap length 40, and establishing near second bladder circumference 42. Furthermore, inelastic retainer 12 constrains elastic self-loosening tether 14 to stretch less than its elastic limit when inflatable bladder 4 is inflated to a pressure sufficient to stop the flow of arterial blood into limb 32 distal to inflatable bladder 4.

Figure 5:
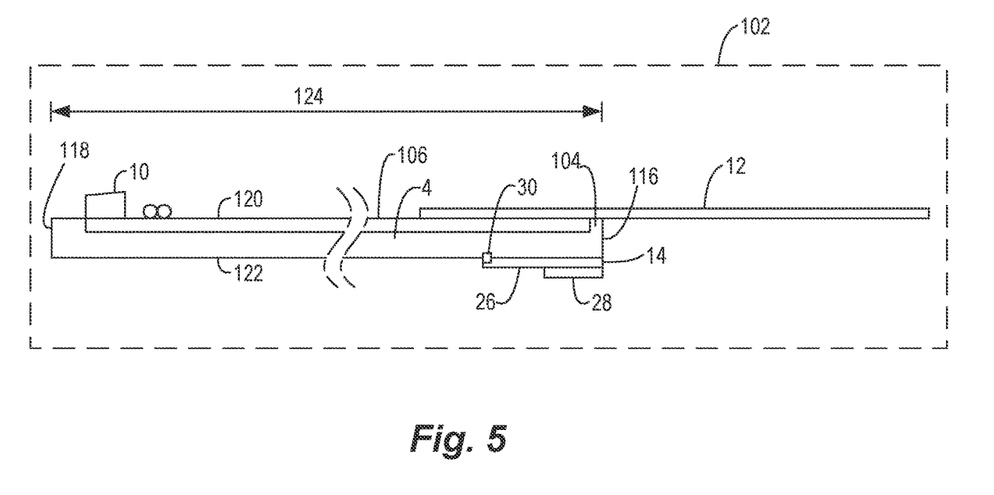
FIG. 5 is the side view of the preferred embodiment having a stiffener.

It is well known in the art that an inflatable bladder may be combined with a stiffener and/or a sheath to form a cuff element. FIG. 5 shows the side view of the preferred embodiment of the safe self-loosening tourniquet cuff having a cuff element that includes an inflatable bladder and a stiffener instead of solely an inflatable bladder.

Safe self-loosening tourniquet cuff assembly 102 includes cuff element 104, port 6, tubing 8, application handle 10, inelastic safety retainer 12, and elastic self-loosening tether 14.

Cuff element 104 includes stiffener 106 inside inflatable bladder 4. Stiffener 106 is non-releasably attached to inflatable bladder 4 to improve cuff stability when the cuff is inflated around a patent's limb, as is well known in prior art. Cuff element 104 includes a first end 116, a second end 118, a top surface 120, and a bottom surface 122. The length between first end 116 and second end 118 defines length 124 of cuff element 104. Length 124 is sufficient for cuff element 104 to overlap upon itself to encircle the patient's limb circumference at a limb location of limb 32.

Inelastic safety retainer 12 is attached to top surface 120 of cuff element 104 near first end 116.

Elastic self-loosening tether 14 is non-releasably attached to bottom surface 122 of cuff element 104 near first end 116. Elastic self-loosening tether 14 is comprised of elastic member 26 and securing member 28. Elastic member 26 is non-releasably attached to bottom surface 122 of cuff element 104 near first end 116 at attachment point 30. Securing member 28 is non-releasably attached to the elastic member 26. Attachment of the securing member 28 to elastic member 26 and elastic member 26 to cuff element 104 may be accomplished through welding, stitching, adhesive or other attachment methods.

In this configuration, elastic self-loosening tether 14 and inelastic safety retainer 12 function as described previously such that cuff element 104 establishes first and second cuff overlap lengths, and establishes first and second cuff circumferences instead of the first and second bladder overlap lengths, and first and second bladder circumferences, respectively, as described earlier for FIGS. 1a-4d.

A prototype of the self-loosening tourniquet cuff was evaluated by the inventors in a pilot clinical study involving 10 human subjects. In this evaluation, a tight application of the prototype cuff was compared to an equally tight application of a standard prior-art cuff. Limb volume change associated with venous congestion was estimated using an accepted method based on air plethysmography that is described in existing clinical literature (see Marcelli et al., referenced above). Using this method, results of this pilot clinical study indicated a reduction of 83.4% in the pressure applied by the uninflated prototype self-loosening cuff compared to standard prior-art cuff, and showed a consistent reduction in all subjects to a level of pressure application well below that associated with significant venous congestion.

In view of the many possible embodiments to which the disclosed principles may be applied, it should be recognized that the illustrated embodiments are only examples and should not be taken as limiting the scope of protection. We therefore claim all that comes within the scope of the following claims.

We claim:

1. A safe self-loosening tourniquet cuff apparatus for enabling optimization of tourniquet time, comprising:
   an inflatable bladder having a length dimension between a first bladder end and a second bladder end sufficient for the inflatable bladder to encircle a patient's limb circumference at a limb location and to overlap itself;
   an elastic self-loosening tether having:
      an elastic member non-releasably attached to the inflatable bladder near the first bladder end;
      a securing member non-releasably attached to the elastic member and adapted to releasably attach to the inflatable bladder when overlapped to establish a first bladder overlap length, wherein the elastic member is adapted for stretching to establish a second bladder overlap length less than the first bladder overlap length and greater than zero; and
   an inelastic safety retainer adapted for retaining the inflatable bladder around the patient's limb near the second bladder overlap length when the inflatable bladder is inflated to a pressure sufficient to stop the flow of arterial blood into the patient's limb distal to the bladder.

2. The apparatus of claim 1 wherein the inelastic safety retainer is further adapted to be operable independently of the elastic self-loosening tether.

3. The apparatus of claim 1 wherein the inelastic safety retainer comprises flexible material that is substantially inelastic when the retained inflatable bladder is inflated to a pressure of less than 600 mmHg.

4. The apparatus of claim 1 wherein the elastic member comprises flexible material having an elastic physical property selected to enable substantially elastic stretching between the first bladder overlap length and the second bladder overlap length.

5. The apparatus of claim 1 wherein the inelastic safety retainer is superposed on the securing member of the elastic self-loosening tether when the inflatable bladder is retained.

6. A safe self-loosening tourniquet cuff assembly, comprising:
   a cuff element having a length dimension between a first end and a second end that is greater than a patient's limb circumference at a limb location and sufficient for the cuff element to encircle the patient's limb and to overlap upon itself;
   an elastic member non-releasably attached to the cuff member near the first end;
   a securing member non-releasably attached to the elastic member and adapted for releasable attachment to the cuff element when overlapped to establish a first cuff circumference less than the limb circumference, thereby applying a first application pressure to the encircled limb by deforming soft tissue of the encircled limb,
   wherein the elastic member is adapted to stretch and thereby self-loosen the cuff element to apply a second application pressure to the encircled limb that is less than the first application pressure and greater than a predetermined minimum application pressure; and
   an inelastic safety retainer operable independently of the elastic member to retain the cuff element at the second application pressure.

7. The self-loosening tourniquet cuff assembly of claim 6, wherein the cuff element includes an inflatable bladder, and wherein the inelastic safety retainer is further operable to retain the cuff element in an overlapped state when the inflatable bladder is inflated to a pressure that is less than a predetermined maximum pressure.

8. The self-loosening tourniquet cuff assembly of claim 7 wherein the predetermined maximum pressure is 600 mmHg.

9. The apparatus of claim 6 wherein the elastic member comprises flexible material selected to enable elastic stretching to establish the second application pressure.

10. A safe self-loosening tourniquet cuff apparatus for enabling optimization of tourniquet time, comprising:
    an inflatable bladder having a length dimension between a first bladder end and a second bladder end that is greater than a patient's limb circumference at a limb location;
    an elastic self-loosening tether having:
       an elastic component non-releasably attached to the inflatable bladder near the first bladder end;
       a securing component non-releasably attached to the elastic component and adapted to releasably attach to the inflatable bladder to establish a first bladder circumference that is less than the limb circumference at the limb location,
       wherein the elastic component is adapted to stretch to establish a second bladder circumference greater than the first bladder circumference and at most equal to the limb circumference at the limb location; and
    an inelastic safety retainer adapted to releasably retain the inflatable bladder near the second bladder circumference when the inflatable bladder is inflated to a pressure sufficient to stop the flow of arterial blood into the patient's limb distal to the bladder.

11. The apparatus of claim 10 wherein the inelastic safety retainer is further adapted for operation independently of the elastic self-loosening tether.

12. The apparatus of claim 10 wherein the inelastic safety retainer comprises flexible material that is substantially inelastic when the inflatable bladder is inflated to a pressure of less than 600 mmHg.

13. The apparatus of claim 10 wherein the elastic member comprises flexible material having an elastic physical property selected to enable substantially elastic stretching between the first bladder circumference and the second bladder circumference.

14. A method for safe self-loosening of a tourniquet cuff, comprising:
    positioning a cuff element at a limb location on a patient, the cuff element having a length dimension between a first end and a second end greater than a limb circumference at the limb location and sufficient for the cuff element to encircle the patient's limb with the first end overlapped over the second end, wherein the cuff member has an elastic member non-releasably attached near the first end and a securing member non-releasably attached to the elastic member;
    releasably attaching the securing member to the cuff element to establish a first cuff circumference less than the limb circumference, thereby applying a first application pressure to the limb by deforming soft tissue of the limb;
    allowing the elastic member to stretch and thereby self-loosen the cuff element, wherein the cuff element in a self-loosened state applies a second application pressure to the limb that is less than the first application pressure and greater than a predetermined minimum application pressure; and extending an inelastic safety retainer over the first end and attaching the inelastic safety retainer to the cuff element for retaining the cuff element at substantially the second application pressure.

\* \* \* \* \*